US008980850B2

(12) United States Patent
Smith

(10) Patent No.: US 8,980,850 B2
(45) Date of Patent: Mar. 17, 2015

(54) ADMINISTRATION OF A NEDD8-ACTIVATING ENZYME INHIBITOR AND HYPOMETHYLATING AGENT

(71) Applicant: Millennium Pharmaceuticals, Inc., Cambridge, MA (US)

(72) Inventor: Peter G. Smith, Arlington, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 13/667,641

(22) Filed: Nov. 2, 2012

(65) Prior Publication Data

US 2013/0116208 A1 May 9, 2013

Related U.S. Application Data

(60) Provisional application No. 61/555,049, filed on Nov. 3, 2011.

(51) Int. Cl.
*A01N 43/04* (2006.01)
*A61K 31/70* (2006.01)
*A61K 31/706* (2006.01)
*A61K 45/06* (2006.01)
*A61K 31/519* (2006.01)

(52) U.S. Cl.
CPC ............... *A61K 31/706* (2013.01); *A61K 45/06* (2013.01); *A61K 31/519* (2013.01)
USPC .................... 514/43; 514/42; 514/45; 514/49

(58) Field of Classification Search
None
See application file for complete search history.

(56) References Cited

U.S. PATENT DOCUMENTS

| | | | |
|---|---|---|---|
| 7,951,810 | B2 | 5/2011 | Critchley et al. |
| 8,207,177 | B2 | 6/2012 | Langston et al. |
| 2008/0057086 | A1 | 3/2008 | Etter |
| 2010/0292177 | A1 | 11/2010 | Armstrong et al. |
| 2010/0311683 | A1 | 12/2010 | Beach et al. |
| 2011/0021544 | A1 | 1/2011 | Armitage et al. |
| 2012/0196823 | A1 | 8/2012 | Tutino et al. |

FOREIGN PATENT DOCUMENTS

| | | | |
|---|---|---|---|
| WO | WO 2004/082619 | A2 | 9/2004 |
| WO | WO 2004/082822 | A2 | 3/2006 |
| WO | WO 2006/034154 | A2 | 3/2006 |
| WO | WO 2006/063111 | A2 | 6/2006 |
| WO | WO 2008/019124 | A1 | 2/2008 |
| WO | WO 2009/139888 | A1 | 11/2009 |
| WO | WO 2013/067043 | A1 | 5/2013 |

OTHER PUBLICATIONS

Teresa A Soucy et al., "An inhibitor of NEDD8-activating enzyme as a new approach to treat cancer," Nature Article, vol. 45819, pp. 732-736 plus Supplemental Information, 2009.

Teresa A. Soucy et al., "Targeting NEDD8-Activated Cullin-RING Ligases for the Treatment of Cancer," Clinical Cancer Research 2009, vol. 15. No. 12, pp. 3911-3916, 2012.

James E. Brownell, "Substrate-Assisted inhibition of Ubiquitin-like Protein-Activating Enzymes: The NEDD8 E1 Inhibitor MLN4924 Forms a NEDD8-AMP Mimetic in Situ," Molecular Cell, vol. 37, pp. 102-111, 2010.

J.S. Kauh et al., "MLN4924, an investigational NEDD8-activating enzyme (NAE) inhibitor, in patients (pts) with advanced solid tumors: Phase I study of multiple treatment schedules," Journal of Clinical Onocolgy, vol. 29, No. 15, 2011.

Ronan T. Swords et al., "Inhibition of NEDD8-activating enzyme: a novel approach for the treatment of acute myeloid leukemia," Blood, vol. 115, No. 18, pp. 3795-3800, 2012.

S. Bhatia et al., "MLN4924, an investigational NEDD8-activating enzyme (NAE) inhibitor, in patients (pts) with metastatic melanoma: Results of a phase I study," Journal of Clinical Oncology, vol. 29, No. 15, 2011.

Milhollen, Michael A., "Azacitidine/Decitabine Synergism with the NEDD8-Activating Enzyme Inhibitor MLN4924 in Pre Clinical AML Models," Presented at the ASH Annual Meeting 2011, Dec. 12, 2011.

Nawrocki, Steffan T. et al., "Disrupting NEDD8-Mediated Protein Turnover with MLN4924 Significantly Augments the Efficacy of Cytarabine," *Blood* (ASH Annual Meeting Abstracts) 2010: 116: Abstract 3255, American Society of Hematology.

Nawrocki, Steffan T. et al., "Disrupting NEDD8-Mediated Protein Turnover with MLN4924 Significantly Augments the Efficacy of Cytarabine," Presented at the ASH Annual Meeting 2010: 116: Abstract 3255, American Society of Hematology (Poster).

Smith, Peter G. et al., "Azacitidine/Decitabine Synergism with the NEDD8-Activating Enzyme Inhibitor MLN4924 in Pre-Clinical AML Models," *Blood* (ASH Annual Meeting Abstracts) 2011: 118: Abstract 578, American Society of Hematology.

Swords, Ronan T. et al., "Inhibition of NEDD8-activating enzyme: a novel approach for the treatment of acute myeloid leukemia," *Blood,* 2010, 115(18) 3796-3800.

Swords, Ronan T. et al., "MLN4924, A Novel First in Class Small Molecule Inhibitor of the Nedd8 Activating Enzyme (NAE), Has Potent Activity in Preclinical Models of Acute Myeloid Leukemia," *Blood* (ASH Annual Abstracts) 2009, 114: Abstract 1021, American Society of Hematology.

Traore, Tary et al. "Synegistic combination of MLN4924, an investigational small molecule inhibitor of NEDD8-activating enzyme (NAE), with azacitidine, a hypomethylating agent, in preclinical AML canser models," Presented at the 17$^{th}$ European Hematology Association Annual Meeting, Jun. 14-17, 2012. Amsterdam, The Netherlands.

(Continued)

*Primary Examiner* — Patrick Lewis

(74) *Attorney, Agent, or Firm* — Finnegan, Henderson, Farabow, Garrett & Dunner

(57) ABSTRACT

The present disclosure relates to methods for the treatment of cancer in patients in recognized need of such treatment. The methods comprise administering to such a patient an NAE inhibitor or a pharmaceutically acceptable salt thereof, such as ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate (MLN4924) or {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate (I-216), and a hypomethylating agent or a pharmaceutically acceptable salt thereof, such as azacitidine or decitabine. Also disclosed are medicaments for use in the treatment of cancer.

30 Claims, 5 Drawing Sheets

(56) References Cited

OTHER PUBLICATIONS

Deangelo, Daniel J., et al., "MLN4924, a novel investigational inhibitor of NEDD8-activating enzyme, in adult patients with acute myeloid leukemia and myelodysplastic syndrome: Results from multiple dosing schedules in a phase 1 study," Presented at the 55th American Society for Hematology Meeting (Dec. 7, 2013) (Poster No. 1443).

Erba, Harry P. et al., "MLN4924, a novel, investigational NEDD8-activating enzyme (NAE) inhibitor, in adult patients with acute myeloid leukemia or high-grade myelodysplastic syndromes: Results from a phase 1 study," Presented at the 16th Congress of the European Hematology Association (Jun. 9-12, 2011) (Poster).

Khalife, Jihane C. et al., "Targeting miR-155 via the NEDD8-Activating Enzyme Inhibitor MLN4924: a Novel Therapeutic Approach for Acute Myeloid Leukemia (AML)," Presented at the American Society for Hematology Meeting (Dec. 9, 2013) (Poster No. 3804).

McDonald, A. et al., "Pharmacodynamic assays demonstrate NAE pathway inhibition following administration of MLN4924 in patients with acute myeloid leukemia," Presented at the 17th Congress of the European Hematology Association (Jun. 14-17, 2012) (poster).

Milhollen; M. A. et al., "Treatment emergent mutations in NAEβ confer resistance to the NEDD8-activating enzyme inhibitor MLN4924," *Cancer Cell* (2012) 21, 388-401.

Milhollen, M. A. et al., "Treatment Emergent Mutations in NAEβ Confer Resistance to the NEDD8-Activating Enzyme inhibitor MLN4924 in pre-clinical DLBCL and AML models," Presented at the 53rd American Society for Hematology Meeting (Dec. 10, 2011) (Poster No. 1413).

Reidy, Mairead et al., "Effect of MLN4924 on TRAIL-Induced Apoptosis in Preclinical Models of Haematological Malignancies," Presented at the 20th European Cell Death Organization Meeting (Sep. 16, 2012) (poster No. P-120).

Sen, Siddhartha et al., "Investigational NEDD8-Activating Enzyme (NAE) Inhibitor, MLN4924, Demonstrates Activity Against Primary AML Blast, Progenitor and Stem Cell Populations," Presented at the 53rd American Society for Hematology Meeting (Dec. 10, 2011) (Poster No. 1414).

Swords, Ronan T. et al., "The Novel, Investigational NEDD8-Activating Enzyme Inhibitor MLN4924 in Adult Patients with Acute Myeloid Leukemia (AML) or High-Grade Myelodysplastic Syndromes (MDS): A Phase 1 Study," Presented at the 53rd American Society for Hematology Meeting (Dec. 6, 2011) (Oral presentation No. 658).

Swords, Ronan T., et al., "MLN494: A Inhibitor of the NEDD8 Activating Enzyme (NAE) has Potent Preclinical Activity Against Acute Myeloid Leukemia," Presented at the 14th Congress of the European Hematology Association (Jun. 4-7, 2009) (poster).

Swords, Ronan T. et al., "Personalized Medicine for Acute Myelogenous Leukemia—At the Entrance Gate," *Am. J. Hematology,* (2011), 86, 631-632.

Swords, Ronan T. et al., "MLN4924, A Novel First in Class Small Molecule Inhibitor of the Nedd8 Activating Enzyme (NAE), Has Potent Activity in Preclinical Models of Acute Myeloid Leukemia," 2010 SUMO, Ubiquitin, UBL Proteins Conference (Feb. 10-13, 2010) (Abstract).

Thomas, Michael P. et al., "MLN4924, an investigational NEDD8-Activating Enzyme inhibitor, induces diferentiation in Acute Myelogenous Leukemia cell lines," 24th EORTC—NCI—AACR Symposium on Molecular Targets and Cancer Therapeutics (Nov. 6-9, 2012) (poster).

Erba, Harry P. et al., "MLN4924, a novel, investigational NEDD8-activating enzyme (NAE) inhibitor, in adult patients with acute myeloid leukemia or high-grade myelodysplastic syndromes: Results from a phase 1 study," Presented at the 16th Congress of the European Hematology Association (Abstract available online as of May 23, 2011) Abstract No. 0068.

McDonald, A. et al., "Pharmacodynamic assays demonstrate NAE pathway inhibition following administration of MLN4924 in patients with acute myeloid leukemia," Presented at the 17th Congress of the European Hematology Association (Abstract available online as of about May 22, 2012), Abstract No. 0084.

Milhollen, M. A. et al., "Treatment Emergent Mutations in NAEβ Confer Resistance to the NEDD8-Activating Enzyme inhibitor MLN4924 in pre-clinical DLBCL and AML models," Presented at the 53rd American Society for Hematology Meeting (Abstract available online as of Nov. 7, 2011).

Millennium: The Takeda Oncology Company and Takeda Pharmaceutical Company Limited "More than Thirty Abstracts on Velcade® and Leading Millennium Pipeline Compounds to be Presented in Oral Sessions at 53rd American Society of Hematology Annual Meeting." News Release available online as of Nov. 8, 2011.

Sen, Siddhartha et al., "Investigational NEDD8-Activating Enzyme (NAE) Inhibitor, MLN4924, Demonstrates Activity Against Primary AML Blast, Progenitor and Stem Cell Populations," Presented at the 53rd American Society for Hematology Meeting (Abstract available online as of Nov. 7, 2011).

Swords, Ronan T. et al., "The Novel, Investigational NEDD8-Activating Enzyme Inhibitor MLN4924 in Adult Patients with Acute Myeloid Leukemia (AML) or High-Grade Myelodysplastic Syndromes (MDS): A Phase 1 Study," Presented at the 52nd American Society for Hematology Meeting (Dec. 6, 2010) (Oral Presentation No. 658).

Swords, Ronan T. et al., "The Novel, Investigational NEDD8-Activating Enzyme Inhibitor MLN4924 in Adult Patients with Acute Myeloid Leukemia (AML) or High-Grade Myelodysplastic Syndromes (MDS): A Phase 1 Study," Presented at the 52nd American Society for Hematology Meeting (Abstract availabe online as of Nov. 2010).

Thomas, Michael P. et al., "MLN4924, an investigational NEDD8-Activating Enzyme inhibitor, induces differentiation in Acute Myelogenous Leukemia cell lines," European Journal of Cancer, vol. 48, Supplement 6, p. 88 (Abstract available online as of about Oct. 31, 2012).

International Preliminary Report on Patentability for International Application No. PCT/US2012/063382 issued Oct. 1, 2014.

International Search Report for International Application No. PCT/US2012/063382 mailed Feb. 1, 2013.

Wang et al., "Targeting protein neddylation: a novel therapeutic strategy for the treatment of cancer", *Expert Opinion Therapeutic Targets,* Mar. 2011, vol. 15, pp. 253-264.

FIG. 1. Combination Index Values

ADMINISTRATION OF A NEDD8-ACTIVATING ENZYME INHIBITOR AND HYPOMETHYLATING AGENT

This application claims benefit of priority from U.S. Provisional Patent Application No. 61/555,049 filed on Nov. 3, 2011.

Inhibition of NEDD8-activating enzyme (NAE) has been shown to induce cancer cell death and inhibit the growth of tumors in xenograft models. See, e.g., T. A. Soucy et al., *Nature,* 2009, 458, 732-737; T. A. Soucy et al., *Clin. Cancer Res.,* 2009, 15 (12), 3912-3916; and J. E. Brownell et al., *Mol. Cell.,* 2010, 37(1), 102-111. Reports of Phase I clinical studies of an NAE inhibitor include R. T. Swords et al., *Blood,* 2010, 115, 3796-3800; J. S. Kauh et al., *Clin. Oncol.,* 2011, 29, abstract 3013; and S. Bhatia et al., *J. Clin. Oncol.,* 2011, 29, abstract 8529. Inhibitors of NAE are described in U.S. patent application Ser. No. 11/346,469 (Publ. No. 2006/0189636, U.S. Pat. No. 7,951,810), U.S. Ser. No. 11/700,614 (Publ. No. 2007/0191293) and U.S. Ser. No. 11/890,338 (Publ. No. 2008/0051404, U.S. Pat. No. 8,008,307), each of the aforementioned publications is hereby incorporated by reference herein in its entirety. If there is any discrepancy between any of these documents and the present specification, the present specification controls.

Hypomethylating agents have been approved by the US Food and Drug Administration in the treatment of cancer. For example, VIDAZA® (azacitidine for injection) is indicated for treatment of patients with the following French-American-British (FAB) myelodysplastic syndromes subtypes: refractory anemia (RA) or refractory anemia with ringed sideroblasts (if accompanied by neutropenia or thrombocytopenia or requiring transfusions), refractory anemia with excess blasts (RAEB), refractory anemia with excess blasts in transformation (RAEB-T), and chronic myelomonocytic leukemia (CMMoL). DACOGEN® (decitabine for injection) is indicated for treatment of patients with myelodysplastic syndromes (MDS) including previously treated and untreated, de novo and secondary MDS of all French-American-British subtypes (refractory anemia, refractory anemia with ringed sideroblasts, refractory anemia with excess blasts, refractory anemia with excess blasts in transformation, and chronic myelomonocytic leukemia) and intermediate-1, intermediate-2, and high-risk International Prognostic Scoring System groups.

The highest possible dose (MTD: maximum tolerated dose) is typically sought for agents for the treatment of cancer because the benefit of the treatment is believed to increase with dose. See, e.g., V, Lin and W. J. Shih, *Biostatistics,* 2001, 2 (2), 203-215, A synergistic combination of agents—that is, a combination of agents that is more effective than is expected from the effectiveness of its constituents, without also compounding the treatment side effects—can provide an opportunity to deliver even greater efficacy at the MTD. Accordingly, it can be desirable to discover synergistic combinations of anti-cancer agents in order to treat cancer patients most effectively, without overloading the patient with side effects.

It has now been discovered that the administration of an NAE inhibitor or a pharmaceutically acceptable salt thereof and a hypomethylating agent or a pharmaceutically acceptable salt thereof provides a synergistic effect. Both in vitro and in vivo synergistic effects were found. In vitro synergy was measured using The Combination Index (M. C. Berenbaum, *J. Theor. Biol.,* 1985, 114, 413-431), as discussed in further detail below. In vivo synergy was measured according to a synergy survival method or a synergy tumor growth method, as discussed in further detail below.

At least one aspect of the present disclosure relates to methods of treating cancer comprising administering to a patient in need of such treatment, a therapeutically effective total amount of an NAE inhibitor or a pharmaceutically acceptable salt thereof and a hypomethylating agent or a pharmaceutically acceptable salt thereof to a subject in need of such treatment.

At least one aspect of the present disclosure is also directed towards the use of an NAE inhibitor or a pharmaceutically acceptable salt thereof with a hypomethylating agent or a pharmaceutically acceptable salt thereof for treating cancer in a patient in need of such treatment.

At least one aspect of the present disclosure relates to a kit comprising at least one medicament for use in treating cancer in a subject in recognized need thereof. For example, the kit may comprise at least one medicament comprising at least one dose of an NAE inhibitor or a pharmaceutically acceptable salt thereof, and instructions for administering the at least one medicament with a hypomethylating agent or a pharmaceutically acceptable salt thereof; or the kit may comprise at least one medicament comprising at least one dose of a hypomethylating agent or a pharmaceutically acceptable salt thereof, and instructions for administering the medicament with an NAE inhibitor or a pharmaceutically acceptable salt thereof. In various embodiments, the kit can comprise at least one medicament comprising at least one dose of an NAE inhibitor or a pharmaceutically acceptable salt thereof and at least one medicament comprising at least one dose of a hypomethylating agent or a pharmaceutically acceptable salt thereof, and instructions for administering the medicaments. Furthermore, for example, the kit can comprise anti-cancer actives consisting of at least one medicament comprising at least one dose of an NAE inhibitor or a pharmaceutically acceptable salt thereof, and at least one medicament comprising at least one dose of a hypomethylating agent or a pharmaceutically acceptable salt thereof; said kit for treating cancer further comprising dosing instructions for administering the medicaments for treatment of the subject in recognized need thereof.

At least one aspect of the present disclosure relates to at least one medicament for use in treating cancer in a subject in need of such treatment. For example, the at least one medicament may comprise an NAE inhibitor or a pharmaceutically acceptable salt thereof, or a hypomethylating agent or a pharmaceutically acceptable salt thereof, or a combination thereof.

At least one aspect of the present disclosure relates to the use of an NAE inhibitor or a pharmaceutically acceptable salt thereof in the manufacture of at least one medicament for treating cancer, wherein the NAE inhibitor or a pharmaceutically acceptable salt thereof is administered with a hypomethylating agent or a pharmaceutically acceptable salt thereof to a patient in need of such treatment.

At least one aspect of the present disclosure relates to the use of a hypomethylating agent or a pharmaceutically acceptable salt thereof in the manufacture of at least one medicament for treating cancer, wherein the a hypomethylating agent or a pharmaceutically acceptable salt thereof is administered with an NAE inhibitor or a pharmaceutically acceptable salt thereof to a patient in need of such treatment.

Figure 1:
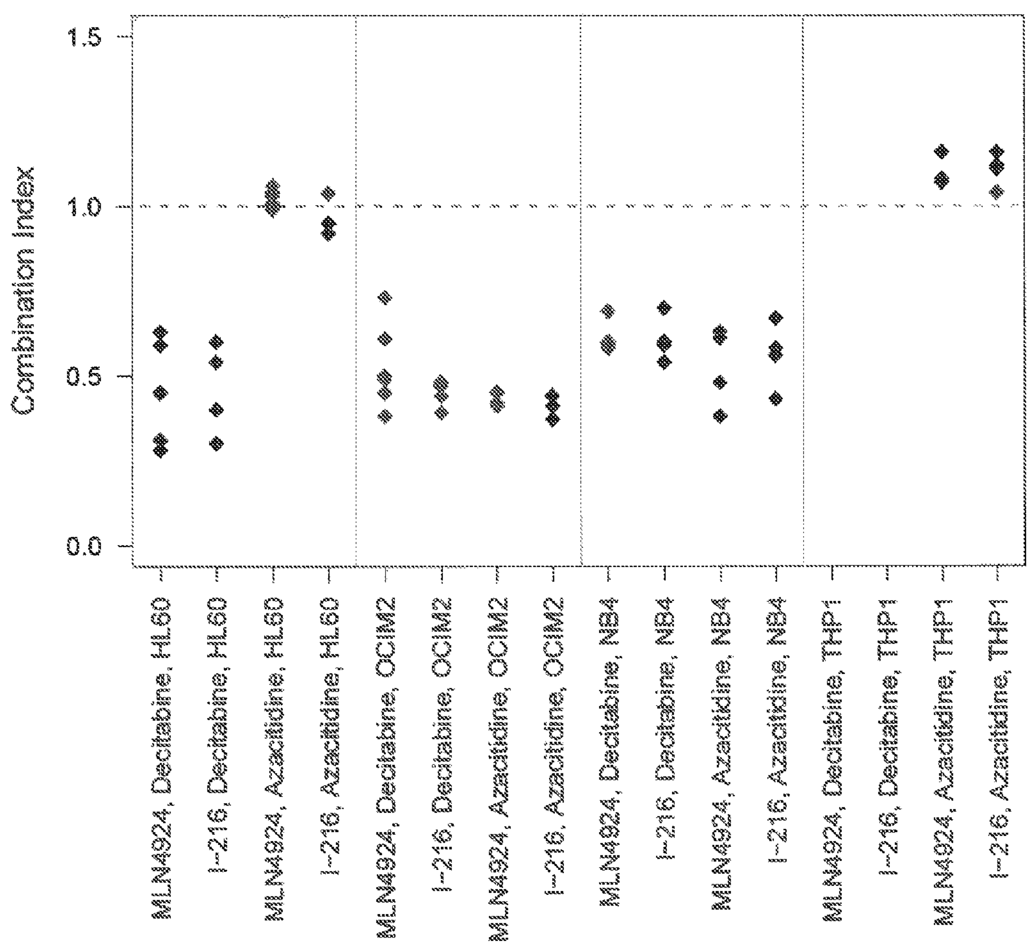
FIG. 1 shows the Combination Index values for NAE inhibitors MLN4924 and I-216, each separately in combination with azacitidine or decitabine in HL60, OCIM2, NB4 and THP-1 cell lines.

The following definitions and abbreviations may be used herein:

ALP alkaline phosphatase
ALT alanine aminotransferase
AML acute myelogenous leukemia
ANC absolute neutrophil count
AST aspartate aminotransferase
AUC area under the plasma concentration versus time curve
BSA body surface area
CR complete response
CRM continual reassessment method
CYP
cytochrome P450
DLBCL diffuse large B-cell lymphoma
DLT dose-limiting toxicity
LFT liver function tests
LVEF left ventricular ejection fraction
MDS myelodysplastic syndromes
MM multiple myeloma
MTD maximum tolerated dose
NAE Nedd8-activating enzyme
NEDD8 neural precursor cell expressed, developmentally down-regulated 8
PASP pulmonary artery systolic pressure
PR partial response
OD once daily
SCLC small cell lung cancer As used herein, "dose-limiting toxicity" (DLT) is defined as a negative event considered by the administering physician to be related to therapy with MLN4924 such that the administering physician believes the doses should be limited in quantity or altogether stopped. Examples of such events include:

- Grade 4 neutropenia (ANC<500 cells/$mm^3$) lasting more than 7 consecutive days
- Grade 3 neutropenia with fever and/or infection, where fever is defined as an oral temperature ≥38.5° C.
- Grade 4 thrombocytopenia (platelets<25,000/$mm^3$ but>10,000/$mm^3$) lasting more than 7 consecutive days
- Grade 3 thrombocytopenia with bleeding
- A platelet count <10,000/$mm^3$ at any time
- Grade 3 or greater nausea and/or emesis despite the use of optimal anti-emetic prophylaxis (wherein "optimal anti-emetic prophylaxis" is defined as an anti-emetic regimen that employs a 5-$HT_3$ antagonist given in standard doses and according to standard schedules), Dexamethasone should not be used because of its CYP3A-inducing effects.
- Grade 3 or greater diarrhea that occurs despite maximal supportive therapy
- An absolute reduction in LVEF of ≥10% to a value <50% (e.g., LVEF=45% in a patient with LVEF=55% at baseline)
- A decrease in LVEF to <40%
- An increase in PASP to >50 mm Hg or 3×baseline
- Any other Grade 3 or greater nonhematologic toxicity with the following exceptions:
  - Grade 3 arthraigia/myalgia
  - Brief (<1 week) Grade 3 fatigue
  - Grade 3 fever that occurs in the absence of Grade 3 or worse neutropenia or documented infection following daily administration of MLN4924
- Treatment delay of more than 1 week because of a lack of adequate recovery of MLN4924-related hematological or nonhernatologic toxicities
- MLN4924-related toxicity that requires that any doses of MLN4924 are missed during a cycle or discontinuation of therapy with MLN4924

As used herein, "clinically effective amount" and "therapeutically effective" means an amount of a therapeutic substance that is sufficient upon appropriate administration over an appropriate period of time to a patient (a) to cause a detectable decrease in the severity of the disorder or disease state being treated; (b) to ameliorate or alleviate the patient's symptoms of the disease or disorder; or (c) to slow or prevent advancement of, or otherwise stabilize or prolong stabilization of, the disorder or disease state being treated (for instance, to prevent additional tumor growth or inhibit the cell growth of a cancer).

When more than one therapeutic substance is being administered, the "clinically effective total amount" or "therapeutically effective total amount" means that the sum of the individual amounts of each therapeutic substance meets the definition of "clinically effective amount" even if the individual amounts of any number of the individual therapeutic substances would not. For example, if 10 mg of A were not a clinically effective amount, and 20 mg of B were not a clinically effective amount, but the administration of 10 mg A+20 mg B resulted in at least one of the results enumerated for the definition of "clinically effective amount," then the sum of 10 mg A+20 mg B would be considered a "clinically effective total amount."

In any form or composition, the administered dose(s) or the clinically effective (total) amount can be expressed as amount (s) of therapeutic substance(s) per patient BSA, e.g., as $mg/m^2$.

As used herein, "patient" means a human being diagnosed with, exhibiting symptoms of or otherwise believed to be afflicted with a disease, disorder or condition and thus in recognized need of the treatment described herein.

As used herein, the illustrative terms "include," "such as," "for example" and the like (and variations thereof, e.g., "includes" and "including," "examples"), unless otherwise specified, are intended to be non-limiting. That is, unless explicitly stated otherwise, such terms are intended to imply "but not limited to," e.g., "including" means including but not limited to.

As used herein, "body surface area" (BSA) is calculated using a standard nomogram, e.g., $$BSA(m^2) = \sqrt{\frac{\text{Ht(cm)} \times \text{Wt(kg)}}{3600}}$$

or $$BSA = \sqrt{\frac{\text{Ht(in)} \times \text{Wt(lb)}}{3131}}$$

Therapeutic Substances—NAE Inhibitors.

The compound ((1S,2S,4R)-4-(4-((1S)-2,3-dihydro-1H-inden-1-ylamino)-7H-pyrrolo[2,3-d]-pyrimidin-7-yl)-2-hydroxycyclopentyl)methyl sulfamate:

MLN4924

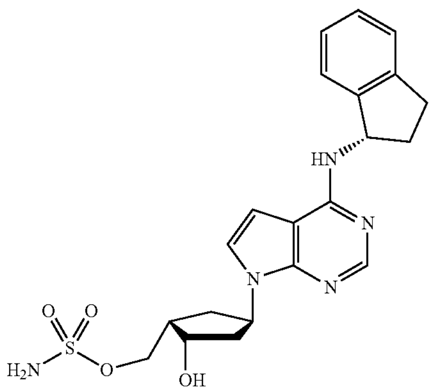

also known as MLN4924, has been reported to be an inhibitor of NEDD8-activating enzyme (NAE). See, e.g., T. A. Soucy et al., *Nature,* 2009, 458, 732-737; T. A. Soucy et al., *Clin. Cancer Res.,* 2009, 15 (12), 3912-3916; and J. E. Brownell et al., *Mol. Cell.,* 2010, 37 (1), 102-111. As discussed above, MLN4924, pharmaceutically acceptable salts thereof, pharmaceutical compositions of MLN4924 or a pharmaceutically acceptable salt thereof, processes for synthesis, and polymorphic forms thereof have been described previously. See, e.g., U.S. patent application Ser. No. 11/700,614 (Publ. No. 2007/0191293), U.S. Ser. No. 12/221,399 (Publ. No. 2009/0036678) and U.S. Ser. No. 12/779,331 (Publ. No. 2011/0021544). MIN4924 Drug Substance ("MLN4924-DS") is the hydrochloride salt of MLN4924, i.e., ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate hydrochloride.

The compound {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate:

I-216

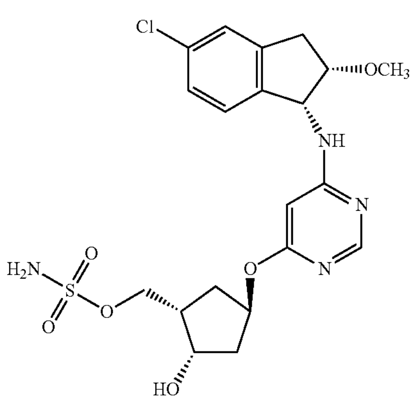

also known as I-216, has also been reported to be an inhibitor of NAE. See U.S. patent application Ser. No. 13/592,389, filed Aug. 23, 2012, claiming priority to U.S. Provisional Patent Appl. No. 61/526,830, filed Aug. 24, 2011, which are hereby incorporated by reference herein in their entirety. If there is any discrepancy between these documents and the present specification, the present specification controls.

Therapeutic Substances—Hypomethylating Agents.

Azacitidine is 4-amino-1-β-D-ribofuranosyl-s-triazin-2(1H)-one (IUPAC name: 4-amino-1-β-D-ribofuranosyl-1,3,5-triazin-2(1H)-one):

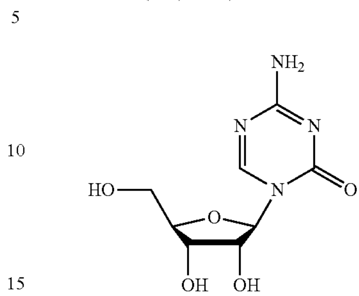

As discussed above, VIDAZA® (azacitidine for injection, Celgene Corporation (Summit, N.J.); VIDAZA® is a registered trademark of Celgene Corporation) is indicated and approved by the US FDA for treatment of patients with the following French-American-British (FAB) myelodysplastic syndromes subtypes: refractory anemia (RA) or refractory anemia with ringed sideroblasts (if accompanied by neutropenia or thrombocytopenia or requiring transfusions), refractory anemia with excess blasts (RAEB), refractory anemia with excess blasts in transformation (RAEB-T), and chronic myelomonocytic leukemia (CMMoL). Full prescribing information for VIDAZA® is available in the commercial package insert.

Decitabine is 4-amino-1-(2-deoxy-β-D-erythropentofuranosyl)-1,3,5-triazin-2(1H)-one:

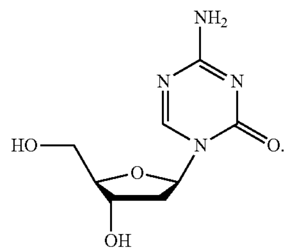

DACOGEN® (decitabine for injection, Eisai, Inc., Woodcliff Lake, N.J.; DACOGEN® is a registered trademark of SuperGen, Inc., Dublin, Calif.) is indicated and approved by the US FDA for treatment of patients with myelodysplastic syndromes (MDS) including previously treated and untreated, de novo and secondary MDS of all French-American-British subtypes (refractory anemia, refractory anemia with ringed sideroblasts, refractory anemia with excess blasts, refractory anemia with excess blasts in transformation, and chronic myelomonocytic leukemia) and intermediate-1, intermediate-2, and high-risk International Prognostic Scoring System groups. Full prescribing information for DACOGEN® is available in the commercial package insert.

Compound Administration

It has now been discovered that the administration of an NAE inhibitor or a pharmaceutically acceptable salt thereof and a hypomethylating agent or a pharmaceutically acceptable salt thereof can provide a synergistic effect.

The NAE inhibitor or a pharmaceutically acceptable salt thereof (NAEi) can be administered in combination with the hypomethylating agent or a pharmaceutically acceptable salt thereof (HMA) in a single dosage form or as a separate dosage form. When administered as a separate dosage form, the hypomethylating agent or a pharmaceutically acceptable salt thereof can be administered prior to, at the same time as, or following administration of the NAE inhibitor or a pharmaceutically acceptable salt thereof. As used herein, the administration in "combination" of NAEi and HMA refers not only to simultaneous or sequential administration of the two agents, but also to the administration of both compounds during a single treatment cycle, as understood by one skilled in the art.

In some embodiments, the present disclosure relates to treating cancer in a patient by administering to the patient an NAE inhibitor or a pharmaceutically acceptable salt thereof (NAEi) and a hypomethylating agent or a pharmaceutically acceptable salt thereof (HMA) according to a 28-day cycle as follows: administer NAEi on Days 1, 4, 8 and 11; and administer HMA on Days 1, 2, 3, 4, 5, 8 and 9. Optionally, the first cycle is 35 days with administration of NAEi on Days 1, 4, 11 and 15 and administration of HMA on Days 8, 9, 10, 11, 12, 15 and 16, with subsequent cycles of 28 days as described in the preceding sentence.

In some embodiments, the present disclosure relates to treating cancer in a patient by administering to the patient an NAE inhibitor or a pharmaceutically acceptable salt thereof (NAEi) and a hypomethylating agent or a pharmaceutically acceptable salt thereof (HMA) according to a 28-day cycle as follows: administer NAEi on Days 1, 3, and 5; and administer HMA on Days 1, 2, 3, 4, 5, 8 and 9. Optionally, the first cycle is 35 days with administration of NAEi on Days 1, 3, and 5 and administration of HMA on Days 8, 9, 10, 11, 12, 15 and 16, with subsequent cycles of 28 days as described in the preceding sentence.

In various embodiments, the NAEi may be ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate ("MLN4924") or {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate ("I-216"). In at least one embodiment, the NAEi is MLN4924. In at least one embodiment, the NAEi is I-216.

In various embodiments, the HMA may be azacitidine or decitabine. In at least one embodiment, the HMA is azacitidine. In at least one embodiment, the HMA is decitabine.

In various embodiments, MLN4924 is administered in combination with azacitidine. In various embodiments, MLN4924 is administered in combination with decitabine. In various embodiments, I-216 is administered in combination with azacitidine. In various embodiments, I-216 is administered in combination with decitabine.

In various embodiments, the NAEi is administered at a dose of about 20 mg/m$^2$, 30 mg/m$^2$, 40 mg/m$^2$, 45 mg/m$^2$, 50 mg/m$^2$, 60 mg/m$^2$ or 75 g/mm$^2$. In various embodiments, the HMA is administered at a dose of about 75 mg/m$^2$.

In various embodiments, the NAEi is administered intravenously. In various embodiments, the NAEi is administered orally. In various embodiments, the NAEi is administered subcutaneously. In various embodiments, the HMA is administered intravenously or subcutaneously.

In some embodiments, the present disclosure relates to treating cancer in a patient by administering to the patient an NAEi and a hypomethylating agent HMA according to a 28-day cycle as follows: administer the NAEi on Days 1, 4, 8 and 11; and administer HMA on Days 1, 2, 3, 4, 5, 8 and 9; wherein the NAEi is MLN4924 and HMA is azacitidine; wherein MLN4924 is administered intravenously at a dose of about 20 mg/m$^2$, 30 mg/m$^2$, 40 mg/m$^2$, 45 mg/m$^2$, 60 mg/m$^2$ or 75 mg/m$^2$; wherein azacitidine is administered at a dose of about 75 mg/m$^2$; and wherein the cancer is a hematologic malignancy. In various embodiments, the hematologic malignancy is acute myeloid leukemia (AML) or myelodysplastic syndromes (MDS). In various embodiments, the hematologic malignancy is AML. In various embodiments, the hematologic malignancy is MDS.

In some embodiments, the present disclosure relates to treating cancer in a patient by administering to the patient an NAEi and a hypomethylating agent HMA according to a 28-day cycle as follows: administer the NAEi on Days 1, 3, and 5; and administer HMA on Days 1, 2, 3, 4, 5, 8 and 9; wherein the NAEi is MLN4924 and HMA is azacitidine; wherein MLN4924 is administered intravenously at a dose of about 20 mg/m$^2$, 30 mg/m$^2$, 40 mg/m$^2$, 45 mg/m$^2$, 50 mg/m$^2$, 60 mg/m$^2$ or 75 mg/m$^2$; wherein azacitidine is administered at a dose of about 75 mg/m$^2$; and wherein the cancer is a hematologic malignancy. In various embodiments, the hematologic malignancy is acute myeloid leukemia (AML) or myelodysplastic syndromes (MDS). In various embodiments, the hematologic malignancy is AML. In various embodiments, the hematologic malignancy is MDS.

Therapeutic Substance: Pharmaceutical Compositions.

The therapeutic substance can be a pharmaceutically acceptable salt. In some embodiments, such salts are derived from inorganic or organic acids or bases. For reviews of suitable salts, see, e.g., Berge et al., *J. Pharm. Sci.*, 1977, 66, 1-19 and *Remington: The Science and Practice of Pharmacy*, 20th Ed., A. Gennaro (ed.), Lippincott Williams & Wilkins (2000).

Examples of suitable acid addition salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

Examples of suitable base addition salts include ammonium salts; alkali metal salts, such as sodium and potassium salts; alkaline earth metal salts, such as calcium and magnesium salts; salts with organic bases, such as dicyclohexylamine salts, N-methyl-D-glucamine; and salts with amino acids such as arginine, lysine, and the like.

For example, Berge lists the following FDA-approved commercially marketed salts: anions acetate, besylate (benzenesulfonate), benzoate, bicarbonate, bitartrate, bromide, calcium edetate (ethylenediaminetetraacetate), camsylate (camphorsulfonate), carbonate, chloride, citrate, dihydrochloride, edetate (ethylenediaminetetraacetate), edisylate (1,2-ethanedisulfonate), estolate (lauryl sulfate), esylate (ethanesulfonate), fumarate, gluceptate (glucoheptonate), gluconate, glutamate, glycollylarsanilate (glycollamidophenylarsonate), hexylresorcinate, hydrabamine (NX-di(dehydro-abietypethylenediamine), hydrobromide, hydrochloride, hydroxynaphthoate, iodide, isethionate (2-hydroxyethanesulfonate), lactate, lactobionate, malate, maleate, mandelate, mesylate (methane-sulfonate), methylbromide, methylnitrate, methylsulfate, mucate, napsylate (2-naphthalenesulfonate), nitrate, pamoate (embonate), pantothenate, phosphate/diphosphate, polygalacturonate, salicylate, stearate, subacetate, succinate, sulfate, tannate, tartrate, teoclate (8-chlorotheophyllinate) and triethiodide; organic cations benzathine (N,N'-dibenzylethylenediamine), chloroprocaine, choline, diethanolamine, ethylenediamine, meglumine (N-methylglucamine) and procaine; and metallic cations aluminum, calcium, lithium, magnesium, potassium, sodium and zinc.

Berge additionally lists the following non-FDA-approved commercially marketed (outside the United States) salts: anions adipate, alginate, aminosalicylate, anhydromethylenecitrate, arecoline, aspartate, bisulfate, butylbromide, camphorate, digluconate, dihydrobromide, disuccinate, glycerophosphate, hemisulfate, hydrofluoride, hydroiodide, methylenebis(salicylate), napadisylate (1,5-naphthalenedisulfonate), oxalate, pectinate, persulfate, phenylethylbarbiturate, picrate, propionate, thiocyanate, tosylate and undecanoate; organic cations benethamine (N-benzylphenethylamine), clemizole (1-p-chlorobenzyl-2-pyrrolildine-1'-ylmethylbenzimidazole), diethylamine, piperazine and tromethamine (tris(hydroxymethyl)aminomethane); and metallic cations barium and bismuth.

As used herein, “pharmaceutically acceptable carrier” refers to a material that is compatible with a recipient subject (a mammal, for instance a human) and is suitable for delivering an active agent to the target site without terminating the activity of the agent. The toxicity or adverse effects, if any, associated with the carrier are, for example, commensurate with a reasonable risk/benefit ratio for the intended use of the active agent.

The pharmaceutical compositions for use in the methods of the present disclosure can be manufactured by methods such as conventional granulating, mixing, dissolving, encapsulating, lyophilizing, or emulsifying processes, among others. Compositions can be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations can contain stabilizers, pH modifiers, surfactants, solubilizing agents, bioavailability modifiers and combinations of these.

Pharmaceutically acceptable carriers that can be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylceliulose, polyacrylates, waxes, polyethylene-polyoxypropylene-block polymers, polyethylene glycol and wool fat.

These pharmaceutical compositions are formulated for pharmaceutical administration to a mammal, such as a human being. Such compositions can be administered orally, parenterally, by inhalation spray, topically, rectally, nasally, buccally, vaginally, or via an implanted reservoir. The term “parenteral” as used herein includes subcutaneous, intravenous, intraperitoneal, intramuscular, intra-articular, intrasynovial, intrasternal, intrathecal, intrahepatic, intralesional and intracranial injection or infusion techniques. In some embodiments, the compositions are administered orally, intravenously, or subcutaneously. In some embodiments, the compositions are administered orally. In some embodiments, the compositions are administered intravenously. These formulations can be designed to be short-acting, fast-releasing, or long-acting. Furthermore, the compositions can be administered in a local rather than systemic means, such as administration (e.g., by injection) at a tumor site.

Pharmaceutical formulations can be prepared as liquid suspensions or solutions using a liquid, such as an oil, water, an alcohol, and combinations of these. Solubilizing agents such as cyclodextrins can be included. Pharmaceutically suitable surfactants, suspending agents, or emulsifying agents, can be added for oral or parenteral administration. Suspensions can include oils, such as peanut oil, sesame oil, cottonseed oil, corn oil and olive oil. Suspension preparations can also contain esters of fatty acids such as ethyl oleate, isopropyl myristate, fatty acid glycerides and acetylated fatty acid glycerides. Suspension formulations can include alcohols, such as ethanol, isopropyl alcohol, hexadecyl alcohol, glycerol and propylene glycol; ethers, such as poly(ethyleneglycol); petroleum hydrocarbons such as mineral oil and petrolatum; and water.

Sterile injectable forms of these pharmaceutical compositions can be aqueous or oleaginous suspensions. These suspensions can be formulated according to techniques known in the art using suitable dispersing or wetting agents and suspending agents, The sterile injectable preparation can also be a sterile injectable solution or suspension in a non-toxic parenterally acceptable diluent or solvent, for example as a solution in 1,3-butanediol. Among the illustrative vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or di-glycerides. Fatty acids, such as oleic acid and its glyceride derivatives are useful in the preparation of injectables, as are natural pharmaceutically-acceptable oils, such as olive oil or castor oil, for instance in their polyoxyethylated versions. These oil solutions or suspensions can also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms can also be used for the purposes of formulation. Compounds can be formulated for parenteral administration by injection such as by bolus injection or continuous infusion. A unit dosage form for injection can be in ampoules or in multi-dose containers.

For example, in various embodiments of the present disclosure, the NAEi is MLN4924 Injection Drug Product (“MLN4924-IDP”). MLN4929-IDP is formulated with the following excipients: citric acid; sodium hydroxide; Cyclodextrin Sulfobutylethers, Sodium Salts (Captisol®); and water for injection. In at least one embodiment, MLN4929-IDP consists of 10 mg/mL MLN4924 (as free base) in a solution containing 50 mM citrate buffer and 100 mg/mL sulfobutylether β-cyclodextrin, pH 3.3.

MLN4924-IDP has experienced stability problems when diluted in saline. MLN4924-IDP can be used for the duration of the retest period indicated on the Certificate of Analysis. In practice, MLN4924-IDP has been stored refrigerated at 5° C.±3° C. Each Type I glass vial nominally contains 5 mL of compounded sterile solution, sealed with a Teflon®-coated butyl rubber stopper and oversealed with an aluminum seal with a plastic Flip-Off® cap.

In various embodiments of the present disclosure, the HMA is azacitidine. Azacitidine is commercially available VIDAZA® (azacitidine for injection), which is supplied as lyophilized powder in 100-mg single-use vials. Refer to the VIDAZA® package insert for additional information.

These pharmaceutical compositions can be orally administered in any orally acceptable dosage form including capsules, tablets, aqueous suspensions or solutions. When aqueous suspensions are required for oral use, the active ingredient can be combined with emulsifying and suspending agents. If desired, certain sweetening, flavoring or coloring agents can also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes, e.g., to mask taste, to affect the site of dissolution or absorption, or to prolong drug action. Coatings can be applied to a tablet or to granulated particles for use in a capsule.

Alternatively, these pharmaceutical compositions can be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

These pharmaceutical compositions can also be administered topically, for instance when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be effected in a rectal suppository formulation (see above) or in a suitable enema formulation. Topically-transdermal patches can also be used. For topical applications, the pharmaceutical compositions can be formulated in a suitable ointment containing the active component suspended or dissolved in one or more carriers. Carriers for topical administration of the compounds of the present disclosure include mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active component(s) suspended or dissolved in at least one pharmaceutically acceptable carrier. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions can be formulated as micronized suspensions in isotonic, pH adjusted sterile saline, or, for instance, as solutions in isotonic, pH adjusted sterile saline, either with our without a preservative such as benzylalkonium chloride. Alternatively, for ophthalmic uses, the pharmaceutical compositions can be formulated in an ointment such as petrolatum.

The pharmaceutical compositions can also be administered by nasal aerosol or inhalation. Such compositions can be prepared according to techniques known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents.

The methods disclosed herein can be used to treat diseases, disorders, and conditions in which inhibition of NAE enzyme activity is detrimental to survival and/or expansion of diseased cells or tissue (e.g., cells are sensitive to NAE inhibition; inhibition of NAE activity disrupts disease mechanisms; reduction of NAE activity stabilizes protein which are inhibitors of disease mechanisms; reduction of NAE activity results in inhibition of proteins which are activators of disease mechanisms). The diseases, disorders and conditions can also include those which require effective cullin and/or ubiquitination activity, which activity can be regulated by diminishing NAE enzyme activity.

For example, the methods disclosed herein can be useful in treatment of disorders involving cellular proliferation, including disorders which require an effective cullin-dependent ubiquitination and proteolysis pathway (e.g., the ubiquitin proteasome pathway) for maintenance and/or progression of the disease state. The methods of the present disclosure can be useful in treatment of disorders mediated via proteins (e.g., NFκB activation, $p27^{Kip}$ activation, $p21^{WAF/CIP1}$ activation, p53 activation) which are regulated by NAE activity. Representative disorders include proliferative disorders, most notably cancers and inflammatory disorders (e.g., rheumatoid arthritis, inflammatory bowel disease, asthma, chronic obstructive pulmonary disease (COPD), osteoarthritis, dermatosis (e.g., atopic dermatitis, psoriasis), vascular proliferative disorders (e.g., atherosclerosis, restenosis) autoimmune diseases (e.g., multiple sclerosis, tissue and organ rejection)); as well as inflammation associated with infection (e.g., immune responses), neurodegenerative disorders (e.g., Alzheimer's disease, Parkinson's disease, motor neuron disease, neuropathic pain, triplet repeat disorders, astrocytoma, and neurodegeneration as result of alcoholic liver disease), ischemic injury (e.g., stroke), and cachexia (e.g., accelerated muscle protein breakdown that accompanies various physiological and pathological states, (e.g., nerve injury, fasting, fever, acidosis, HIV infection, cancer affliction, and certain endocrinopathies)).

The methods disclosed herein can be useful, for instance, for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes solid tumors and bloodborne tumors. The term "cancer" encompasses diseases of skin, tissues, organs, bone, cartilage, blood, and vessels. The term "cancer" further encompasses primary and metastatic cancers.

In some embodiments, the cancer is a solid tumor. Examples of solid tumors that can be treated by the methods of the present disclosure include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., small cell lung cancer (SCLC), non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In some embodiments, the cancer is a hematologic malignancy. Examples of hematologic malignancy include acute myeloid leukemia (AML); chronic myelogenous leukemia (CML), including accelerated CML and CML blast phase (CML-BP); acute lymphoblastic leukemia (ALL); chronic lymphocyte leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes.

In some embodiments, a physician may diagnose a patient with a cancer as predominantly one type. In some embodiments, a physician may diagnose a patient as having more than one type of cancer. In some embodiments, the diagnosis is predominantly one type of myelodysplastic syndromes. In some embodiments, the diagnosis is more than one type of myelodysplastic syndromes.

In some embodiments, methods of the present disclosure are used to treat a patient having, or at risk of developing or experiencing, a recurrence in a tumor cancer, such as colorectal cancer, ovarian cancer, lung cancer, breast cancer, gastric cancer, prostate cancer and pancreatic cancer. In some embodiments, methods of the present disclosure are used to treat a patient having, or at risk of developing or experiencing, a recurrence in a hematologic cancer, such as AML, CML, CML-BP, ALL, or CLL.

In order that this disclosure be more fully understood, the following examples are set forth. These examples are illustrative only and are not intended to limit the scope of the present disclosure in any way.

EXAMPLES 1. in vitro Cell Viability Assays

The experimental protocol used Poly-D-lysine BioCoat™ Black/Clear 384 plates (Becton Dickinson, Franklin Lakes, N.J.). The appropriate NAE inhibitor was dissolved in DMSO and delivered into the wells using an Echo (Labcyte, Sunnyvale, Calif.) liquid handling system. HL60 and THP-1 lines were obtained from ATCC (American Type Culture Collection, Manassas, Va.), while NB4 and OCI-M2 lines were obtained from DSMZ (Deutsche Sammlung von Mikroorganismen und Zellkulturen GmbH, Brunswick, Germany). Each plate had a cell suspension from one of the lines added to the wells. A portion of the wells were used as positive controls (no compound was added), while another portion of the wells were used as negative controls (no cells were added). The plates were incubated for 72 hours, and then the cell viabilities were measured using an ATPlite (PerkinElmer, Waltham, Mass.) assay.

Statistical Analyses.

Normalization. The viability data was normalized separately for each plate by scaling the data so that the median of the negative controls was 0 and the median of the positive controls was 100. More formally, $$V_i = 100\frac{U_i - \text{median}(U_-)}{\text{median}(U_+) - \text{median}(U_-)}$$

where $V_i$ is the normalized viability of the $i^{th}$ well, $U_i$ is the raw viability measurement, median($U_-$) is the median of the negative controls, and median($U_+$) is the median of the positive controls. After normalization, the controls were discarded.

Response Surface Model and Fitting.

A response surface model was used to describe the relationship between the normalized viability and the drug concentrations. For a given plate, let $$C=(C_A/I_1)+(C_B/I_2)$$

$$x=(C_A/I_1)/C$$

$$E_{max}=E_1+E_2+E_3x^2+E_4x^3$$

$$I=1+I_3x(1-x)$$

$$S=S_1+S_2x+S_3x^2+S_4x^3$$

$$V=100-E_{max}(1+(I/C)^S)^{-1}+\text{error}$$

where $E_1$, $E_2$, $E_3$, $E_4$, $I_1$, $I_2$, $I_3$, $S_1$, $S_2$, $S_3$, and $S_4$ are parameters, $C_A$ and $C_B$ are the respective concentrations of drugs A and B, and V is the normalized viability measurement. It was assumed that the error values were independent and identically distributed normal random variables. This model is an extension of the Hill equation (A. V. Hill, *J. Physiol.,* 1910, 40, iv-vii), which is commonly used to model the effect of a single drug. The data were fitted to this model using the maximum likelihood method with the statistical software program R R Development Core Team (2008) (R: A language and environment for statistical computing. R Foundation for Statistical Computing, Vienna, Austria. ISBN 3-900051-07-0, URL http://www.R-project.org).

Quality Checks.

Three types of quality checks were applied to the plates. First, it was checked that the variation of the positive controls and the mean of the negative controls were small. Next, it was checked that the new data agreed with data from previous single drug experiments. Finally, the residuals from the response surface fit were analyzed to ensure that the residual sum of squares was sufficiently small. All of these quality checks were based on numerical thresholds to make pass/fail decisions, and the same thresholds were used for all of the plates in the experiment. If a plate failed any one of the quality checks, it was removed from the analysis.

Measuring in vitro Synergy.

The Combination Index (M. C. Benenbaumo, *J. Theor. Biol.,* 1985, 114, 413-431) was used as a measure of drug synergy. The Combination Index is computed based on an isobologram, which is a slice of the dose response surface with constant viability. For the present analysis, the 50% isobologram, which is the dose contour that has 50% viability, was used. The $EC50_A$ and $EC50_B$ are defined be the respective doses of drugs A and B alone that have a viability of 50%. For a point ($D_A$, $D_B$) along the 50% isobologram, the Combination Index is defined as $(D_A/EC50_A)+(D_B/EC50_B)$. Since the choice of ($D_A$, $D_B$) can be arbitrary, the constraint $D_A/D_B=EC50_A/EC50_B$ was used. If the Combination Index is less than 1, it indicates that the isobologram curves inward, and that the drug combination is synergistic. Conversely, if the Combination Index is greater than 1, the 50% isobologram curves outward, indicating antagonism. In the more stringent analysis method applied according to the present disclosure, Combination Index values within the range 0.8-1.2 are considered additive. This rule prevents small deviations from additivity from being classified as synergistic.

A two sided t-test for each condition was performed to determine if the mean Combination Index differed from 1. The Benjamini-Hochberg method (Y. Benjamini and Y. Hochberg, *J. R. Stat. Soc., Series B* (*Stat. Methadol.*), 1995, 57 (1), 289-300) was used to adjust the resulting p-values for multiple hypothesis testing. An adjusted p-value below 0.05 was considered to statically significant. In order for a combination to be classified as synergistic, we required that three criteria be met: the mean Combination Index for the condition had to be less than 1, the difference had to be statistically significant, and Combination Index had to be outside the range (0.8, 1.2). This third criterion prevented small deviations from additivity from being classified as synergistic. Combinations for which the p-value was above 0.05 or the Combination Index was within the range (0.8, 1.2) were classified as additive.

Cell viability assays were used to assess the combination effect in vitro of each of two NAE inhibitors, MLN4924 and I-216, with each of two hypomethylating agents, azacitidine and decitabine, in four cell lines, HL60, OCIM2, NB4, and THP-1. FIG. 1 shows the Combination Index for all of the experiments that passed the quality checks among each tested combination. The results are arranged by the condition. Table 1, below, lists the mean Combination Index, the adjusted p-value, and the conclusion for each determined combination. As Table 1 shows, all eight combinations of NAE inhibitor and hypomethylating agent demonstrated a synergistic effect in both the OCIM2 and NB4 cell lines. In the HL60 line, both NAE inhibitors demonstrated synergy with decitabine and showed an additive effect with azacitidine. In the THP-1 line, both NAE inhibitors demonstrated an additive effect with azacitidine. Due to the lack of single agent activity of decitabine in THP-1, a Combination Index cannot be calculated for the in vitro experiments with NAE inhibitors and decitabine in THP-1.

TABLE 1

Summary of the Combination Index values.

| NAE inhibitor | Hypomethylating agent | Cell line | Number of passing plates | Mean Combination Index | Adjusted P-value | Conclusion |
|---|---|---|---|---|---|---|
| MLN4924 | Decitabine | HL60 | 6 | 0.45 | $6.2 \times 10^{-4}$ | Synergy |
| I-216 | Decitabine | HL60 | 4 | 0.46 | $5.8 \times 10^{-3}$ | Synergy |
| MLN4924 | Azacitidine | HL60 | 5 | 1.03 | $1.1 \times 10^{-1}$ | Additivity |
| I-216 | Azacitidine | HL60 | 3 | 0.97 | $4.9 \times 10^{-1}$ | Additivity |
| MLN4924 | Decitabine | OCIM2 | 7 | 0.52 | $1.4 \times 10^{-4}$ | Synergy |
| I-216 | Decitabine | OCIM2 | 5 | 0.45 | $4.0 \times 10^{-5}$ | Synergy |
| MLN4924 | Azacitidine | OCIM2 | 5 | 0.44 | $4.8 \times 10^{-6}$ | Synergy |
| I-216 | Azacitidine | OCIM2 | 3 | 0.41 | $2.7 \times 10^{-3}$ | Synergy |
| MLN4924 | Decitabine | NB4 | 5 | 0.61 | $1.4 \times 10^{-4}$ | Synergy |
| I-216 | Decitabine | NB4 | 4 | 0.61 | $2.7 \times 10^{-3}$ | Synergy |
| MLN4924 | Azacitidine | NB4 | 4 | 0.52 | $5.8 \times 10^{-3}$ | Synergy |
| I-216 | Azacitidine | NB4 | 4 | 0.56 | $5.3 \times 10^{-3}$ | Synergy |
| MLN4924 | Decitabine | THP-1 | 4 | NA | NA | NA |
| I-216 | Decitabine | THP-1 | 4 | NA | NA | NA |
| MLN4924 | Azacitidine | THP-1 | 4 | 1.10 | $2.4 \times 10^{-2}$ | Additivity |
| I-216 | Azacitidine | THP-1 | 4 | 1.11 | $2.7 \times 10^{-2}$ | Additivity |

FIG. 1 shows the Combination Index values for each plate, arranged by the condition (i.e., a given drug combination applied to a given cell line). These results were summarized by computing the mean Combination Index for each condition, as shown in Table 1.

2. in vivo Tumor Efficacy Models.

Subcutaneous Xenograft Models

Test subjects. HL-60 ($2\times10^6$) tumor cells in 100 μl phosphate buffered saline with Matrigel™ (BD Biosciences, Bedford, Mass.) were aseptically injected into the subcutaneous space in the right dorsal flank of female Ncr nude mice (age 5-8 weeks, Charles River Laboratories, Wilmington, Mass.) using a 26-gauge needle. THP-1 ($2.5\times10^6$) or OCI-M2 ($5\times10^6$) tumor cells in 100 phosphate buffered saline with Matrigel™ were aseptically injected into the subcutaneous space in the right dorsal flank of female CB.17 SCID mice (age 5-8 weeks, Charles River Laboratories) using a 26-gauge needle.

Figure 2:
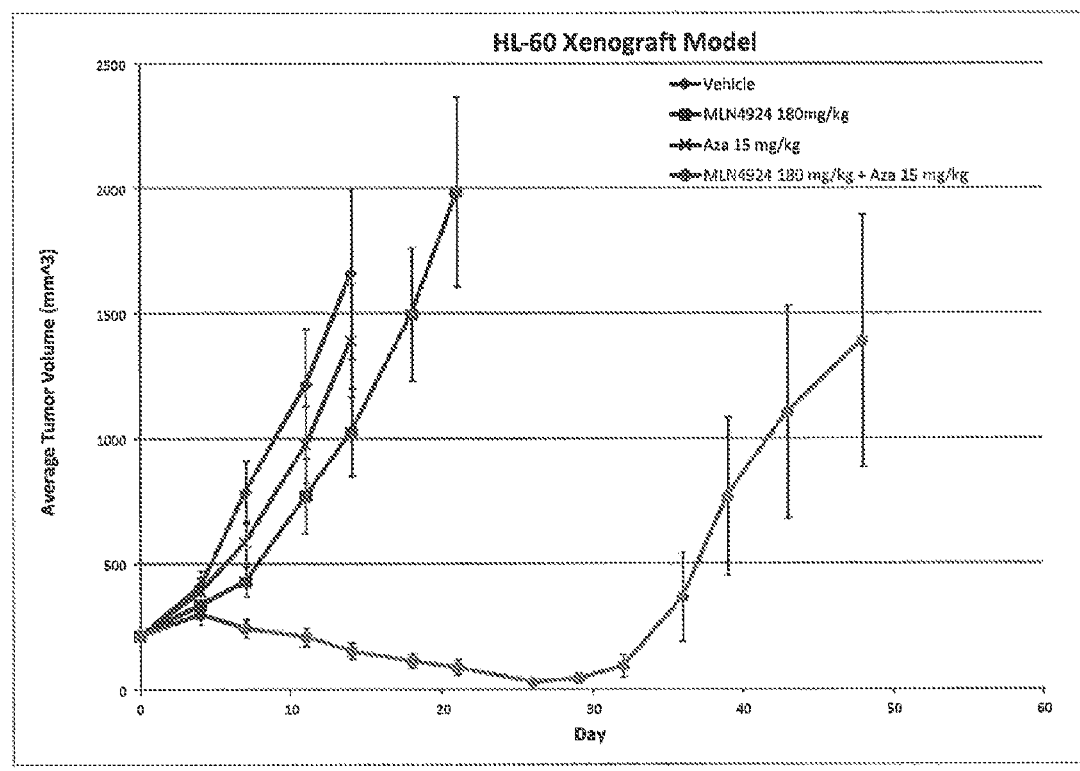
FIG. 2 shows a plot of tumor volume as a function of time in an HL-60 subcutaneous xenograft model following subcutaneous treatment with: the vehicle alone, MLN4924 as a single agent, azacitidine ("Aza") as a single agent, and co-administration (s.c.) of MLN4924 and azacitidine, on Days 1, 4, 8, 11, 15 and 18 at the indicated doses.
Figure 3:
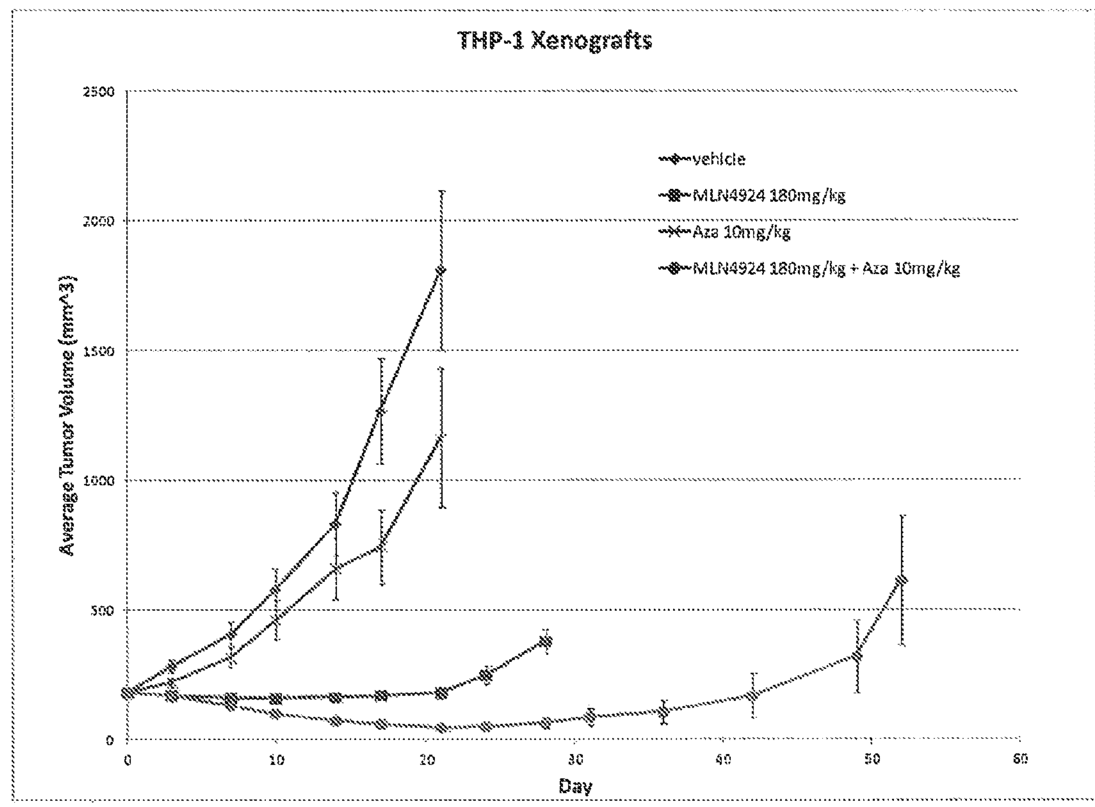
FIG. 3 shows a plot of tumor volume as a function of time in a THP-1 subcutaneous xenograft model following subcutaneous treatment with: the vehicle alone, MLN4924 as a single agent, azacitidine ("Aza") as a single agent, and co-administration (s.c.) of MLN4924 and azacitidine, on Days 1, 4, 8, 11, 15 and 18 at the indicated doses.
Figure 4:
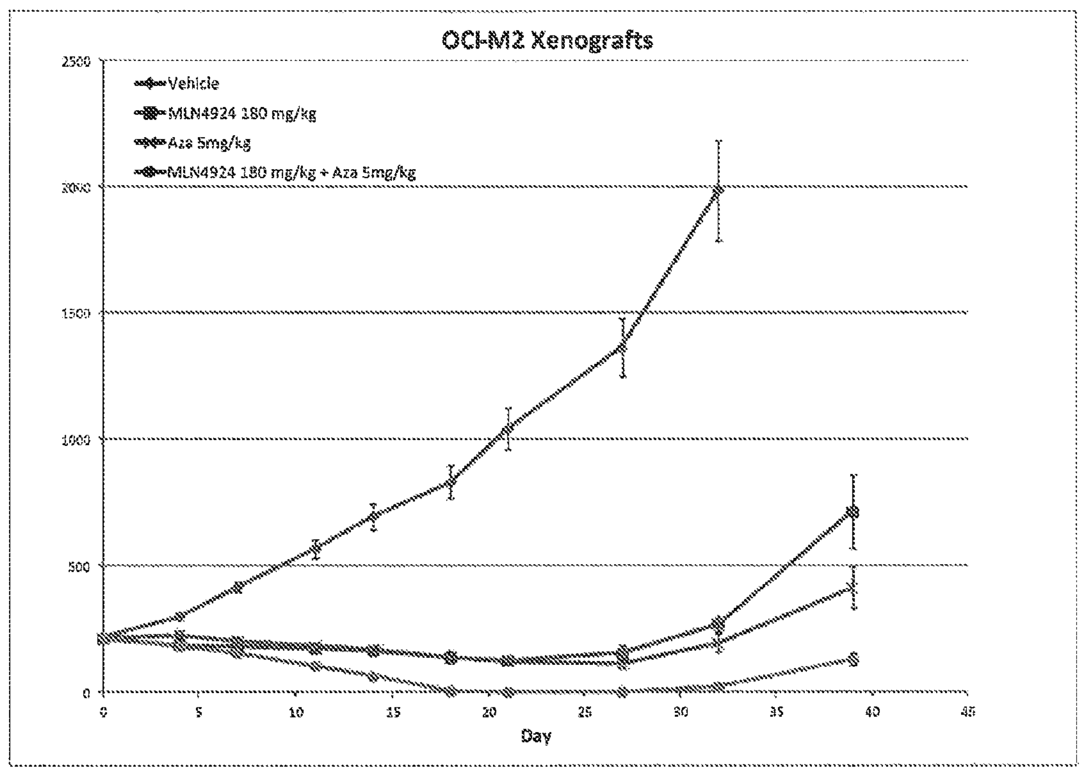
FIG. 4 shows a plot of tumor volume as a function of time in a OCI-M2 subcutaneous xenograft model following subcutaneous treatment with: the vehicle alone, MLN4924 as a single agent, azacitidine ("Aza") as a single agent, and co-administration (s.c.) of MLN4924 and azacitidine, on Days 1, 4, 8, 11, 15 and 18 at the indicated doses.

Beginning on day seven (7) after inoculation, tumors were measured twice weekly using a vernier caliper. Tumor volumes were calculated using standard procedures (0.5×(length×width)). When the tumors reached a volume of approximately 200 $mm^3$, mice were randomized into groups of 10 and injected subcutaneously with compound inhibitor (200 μl) at various doses and schedules, with the first dosing day defined as Day 1. All control groups received vehicle alone. Tumor size and body weight were measured approximately twice a week for the duration of the study. Mice were euthanized when their tumor volume reached 10% of their body weight, or when the average tumor volume of a treatment or control group reached approximately 2000 $mm^3$. The dosing schedule for each study was as follows: MLN4924 and azacitidine were dosed separately or co-dosed by subcutaneous injection on Days 1, 4, 8, 11, 15 and 18 at the indicated doses. Tumor growth continued to be monitored after the dosing period. Average tumor volume reported as a function of time is shown in FIG. 2-4.

Statistical Analyses of Synergy for Tumor Growth in Subcutaneous Xenograft Models.

For the THP-1 and OCI-M2 models, measurements from day 0 to 21 were analyzed. For the HL60 model, measurements from day 0 to 14 were used, since several of the mice had tumors exceeding the allowed volume after day 14. All tumor volumes had a value of 1 added to them before $\log_{10}$ transformation. These values were compared across treatment groups to assess whether the differences in the trends over time were statistically significant. To compare pairs of treatment groups, the following mixed-effects linear regression model was fit to the data using the maximum likelihood method:

$$Y_{ijk}-Y_{10k}=Y_{10k}+\text{treat}_i+\text{day}_j+\text{day}_j^2+(\text{treat}*\text{day})_{ij}+(\text{treat}*\text{day}^2)_{ij}+e_{ijk}$$

where $Y_{ijk}$ is the $\log_{10}$ tumor value at the $j^{th}$ point of the $k^{th}$ animal in the $i^{th}$ treatment, $Y_{10k}$ is the day 0 $\log_{10}$ tumor value in the $k^{th}$ animal in the $i^{th}$ treatment, $\text{day}_j$ was the median-centered time point and was treated as a continuous variable, and $e_{ijk}$ is the residual error. A spatial power law covariance matrix was used to account for the repeated measurements on the same animal over time. Interaction terms as well as $\text{day}_j^2$ terms were removed if they were not statistically significant.

A likelihood ratio test was used to assess whether a given pair of treatment groups exhibited differences which were statistically significant. The −2 log likelihood of the full model was compared to one without any treatment terms (reduced model) and the difference in the values was tested using a Chi-squared test. The degrees of freedom of the test were calculated as the difference between the degrees of freedom of the full model and that of the reduced model.

In addition to the statistical significance, a measure of the magnitude of the effect for each treatment was found. The predicted differences in the log tumor values ($Y_{ijk}$-$Y_{10k}$) vs. time were taken from the above model to calculate mean area under the curve (AUC) values for each treatment group. A dAUC value was then calculated as:

$$dAUC = 100\frac{\text{mean}(AUC_{control}) - \text{mean}(AUC_{treatment})}{|\text{mean}(AUC_{control})|}$$

For synergy analyses, the observed differences in the log tumor values were used to calculate AUC values for each animal. In instances when an animal in a treatment group was removed from the study, the last observed tumor value was carried forward through all subsequent time points. To improve the robustness of the synergy analysis, the following procedure was applied to the AUC values from each treatment group. Let x be the set of AUC values for a given treatment group. A range of interest was defined:

$$(\text{median}(x)-5*\text{MAD}(x),\ \text{median}(x)+5*\text{MAD}(x)).$$

Here, MAD is the median absolute deviation of x. If any value in x fell outside this range, that value was replaced by the value at the closest boundary. The procedure was non-iterative, so the range was computed only once for each treatment group.

The synergy score for the combination of treatments A and B was defined as $$100*(\text{mean}(AUC_{AB})=\text{mean}(AUC_A)-\text{mean}(AUC_B)+\text{mean}(AUC_{ctl}))/\text{mean}(AUC_{ctl})$$

where $AUC_{AB}$, $AUC_A$, $AUC_B$, and AUC are the $AUC_{ctl}$ values for animals in the combination group, the A group, the B group, and the control group, respectively. The standard error of the synergy score was computed based on the variation in the AUC values among the animals. A two sided t-test was used to determine if the synergy score was significantly different from zero. If the P-value was below 0.05, and the synergy score was less than zero, then the combination was considered to be synergistic. If the P-value was above 0.05, then the combination was considered to be additive.

Mouse xenograft models were used to assess the combination effect in vivo of NAE inhibitor MLN4924 and hypomethylating agent azacitidine, FIGS. 2-4 show tumor volume as a function of time in three subcutaneous xenograft models following treatment with the vehicle as a single agent, MLN4924 as a single agent, azacitidine ("Aza") as a single agent, and co-administration (s.c.) of MLN4924 and azacitidine on Days 1, 4, 8, 11, 15 and 18 at the indicated doses.

In the HL-60 subcutaneous xenograft model (FIG. 2), MLN4924 and azacitidine as single agents had a marginal effect on tumor growth. In contrast, co-dosing MLN4924 and azacitidine led to tumor regressions, with a statistical assessment of synergy.

In the THP-1 xenograft model (FIG. 3), azacitidine as single agent had a marginal effect on tumor growth whereas MLN4924 as a single agent inhibited tumor growth. In contrast, co-dosing MLN4924 and azacitidine led to tumor regressions. Despite the statistical assessment of additivity in this model, rather than synergy, the figure clearly shows a combination benefit: tumor growth inhibition (single agent) versus tumor regression with the combination.

An additional demonstration of improved activity in THP-1 is the delay in tumor regrowth with the combination compared to each single agent. The additional benefit provided by the combination over the single agent treatments was statistically significant, as shown in Table 3b (P-value <0.05).

In the OCI-M2 subcutaneous xenograft model (FIG. 4), MLN4924 and azacitidine as single agents inhibited tumor growth. In contrast, co-dosing MLN4924 and azacitidine led to tumor regressions with a statistical assessment of synergy.

Disseminated Xenograft Model

Figure 5:
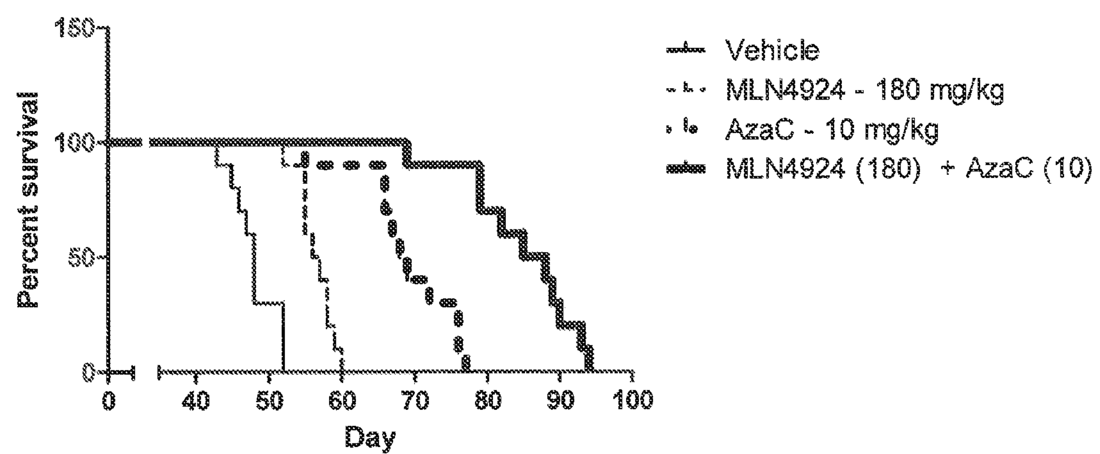
FIG. 5 shows a plot of percentage survival as a function of time in an HL60 disseminated model following subcutaneous treatment with: the vehicle alone, MLN4924 as a single agent, azacitidine ("AzaC") as a single agent, and co-administration (s.c.) of MLN4924 and azacitidine on Days 22, 25, 29, 32, 36, 39 at the indicated doses.

Test subjects. HL-60 ($1\times10^7$) tumor cells in 100 μL IMDM media were inoculated in the lateral vein of female mice CB-17 SCID (age 8-10 weeks, Charles River Laboratories, Wilmington, Mass.) using a 27-gauge needle. On day 20 post-inoculation, mice were randomized into groups of 10. Starting on day 22, mice were dosed subcutaneously with vehicle, 180 mg/kg MLN4924, 10 mg/kg azacitidine, or the combination of 180 mg/kg MLN4924 and 10 mg/kg azacitidine, using the same twice-weekly schedule as described in the subcutaneous xenograft experiments (dosing on days 22, 25, 29, 32, 36, 39). The mice were monitored at least twice weekly for body weight loss and signs of disease, including paresis or paralysis of hind limbs and emergence of palpable and internal solid tumors. The day on which an animal died or was sacrificed due to disease burden was recorded. Survival time is shown in FIG. 5.

Statistical Analysis of Synergy for Survival in Disseminated Xenograft Model.

To determine synergy in the survival times, the mean survival times and corresponding standard errors were computed for each treatment group. The survival synergy was defined as $$\text{mean}(\text{survival}_{AB})-\text{mean}(\text{survival}_A)-\text{mean}(\text{survival}_B)+\text{mean}(\text{survival}_{ctl})$$

where $\text{survival}_{AB}$, $\text{survival}_A$, $\text{survival}_B$, and $\text{survival}_{ctl}$ are the survival times for animals in the combination group, the A group, the B group, and the control group, respectively. The standard error for the survival synergy was found by adding the standard error of each of the four terms in quadrature. A two sided Z-test was used to determine if the survival synergy was significantly different from zero. If the P-value was below 0.05, and the survival synergy was greater than zero, then the combination was considered to be synergistic. If the P-value was above 0.05, then the combination was considered to be additive.

FIG. 5 shows survival as a function of time in a disseminated xenograft model in which HL-60 cells were inoculated by intravenous injection, and mice were treated with vehicle, with MLN4924 as a single agent, azacitidine as a single agent, and co-administration of s.c. MLN4924 and azacitidine beginning on Day 22 post-inoculation at the indicated doses, using the same twice-weekly schedule as in the experiments in FIGS. 2-4. In the HL-60 disseminated model (FIG. 5), MLN4924 and azacitidine as single agents both extended mean survival time compared to the control group (8.4 day extension for MLN4924 and 21.1 day extension for azacitidine). The combination of MLN4924 and azacitidine extended mean survival time by 36.7 days, which is 7.2 days longer than would be expected from an additive combination (FIG. 5). The survival synergy was statistically significant.

TABLE 2a

Synergy assessment for HL60 subcutaneous xenograft tumors.

| Treatment | Synergy score | Synergy score standard error | P-Value | Assessment |
|---|---|---|---|---|
| MLN4924 180 mg/kg + azacitidine 15 mg/kg | −54.8 | 17.6 | 0.005 | Synergy |

TABLE 2b

Pairwise comparison of treatment groups for HL60 subcutaneous xenograft tumors.

| Reference | Treated | dAUC | P-Value for the difference in effects |
|---|---|---|---|
| MLN4924 180 mg/kg | MLN4924 180 mg/kg + azacitidine 15 mg/kg | 118.3 | <0.001 |
| azacitidine 15 mg/kg | MLN4924 180 mg/kg + azacitidine 15 mg/kg | 112.9 | <0.001 |

TABLE 3a

Synergy assessment for THP-1 subcutaneous xenograft tumors.

| Treatment | Synergy score | Synergy score standard error | P-Value | Assess |
|---|---|---|---|---|
| MLN4924 180 mg/kg + azacitidine 10 mg/kg | −40.5 | 21.4 | 0.078 | Additive |

TABLE 3b

Pairwise comparison of treatment groups for THP-1 subcutaneous xenograft tumors.

| Reference | Treated | dAUC | P-Value for the difference in effects |
|---|---|---|---|
| MLN4924 180 mg/kg | MLN4924 180 mg/kg + azacitidine 10 mg/kg | 882.2 | <0.001 |
| azacitidine 10 mg/kg | MLN4924 180 mg/kg + azacitidine 10 mg/kg | 221.1 | <0.001 |

TABLE 4a

Synergy assessment for OCI-M2 subcutaneous xenograft tumors.

| Treatment | Synergy score | Synergy score standard error | P-Value | Assessment |
|---|---|---|---|---|
| MLN4924 180 mg/kg + azacitidine 5 mg/kg | −52.1 | 15.1 | 0.002 | Synergy |

TABLE 4b

Pairwise comparison of treatment groups for OCI-M2 subcutaneous xenograft tumors.

| Reference | Treated | dAUC | P-Value for the difference in effects |
|---|---|---|---|
| MLN4924 180 mg/kg | MLN4924 180 mg/kg + azacitidine 5 mg/kg | 545.5 | <0.001 |
| azacitidine 5 mg/kg | MLN4924 180 mg/kg + azacitidine 5 mg/kg | 767.6 | <0.001 |

TABLE 5a

Mean survival times for mice with HL-60 disseminated xenograft model.

| Treatment | Mean survival time (days) | Standard error of mean survival time (days) |
|---|---|---|
| Vehicle | 48.1 | 1.0 |
| MLN4924 180 mg/kg | 56.5 | 0.7 |
| azacitidine 10 mg/kg | 69.2 | 2.1 |
| MLN4924 180 mg/kg + azacitidine 10 mg/kg | 84.8 | 2.4 |

TABLE 5b

Survival time synergy assessment for HL-60 disseminated xenograft model.

| Treatment | Survival synergy (days) | Survival synergy standard error (days) | P-Value | Assess |
|---|---|---|---|---|
| MLN4924 180 mg/kg + azacitidine 10 mg/kg | 7.2 | 3.4 | 0.036 | Synergy |

Prophetic Drug Administration Example.

Prior to use, MLN4924-IDP vials are warmed to ambient conditions (15° C. to 30° C.) by placing them at room temperature. Accelerated warming methods, such as a water bath, was not, and must not be, used. MLN4924-IDP is stable at room temperature for 8 hours prior to dilution.

Each MLN4924-IDP vial contains nominally 5 mL (50 mg MLN4924 as free base). Using sterile technique, the appropriate volume of drug is withdrawn from vial(s) and injected into a 250 mL IV bag containing a 5% dextrose solution, which is then gently inverted repeatedly to mix. The prepared MLN4924-IDP IV bag must be used within 6 hours if stored at room temperature. Alternatively, the prepared IV bag is chemically stable and can be stored for up to 24 hours at 5° C.±3° C. After 24 hours of storage at 5° C.±3° C., the prepared IV bag must be used within 6 hours upon coming to room temperature. The vial must not be shaken at any time during dose preparation.

Instructions for the preparation, reconstitution, and dispensation of azacitidine are provided in the azacitidine) (VIDAZA®) package insert The amount of MLN4924 and azacitidine administered is based on body surface area (BSA). BSA is calculated using a standard nomogram on Cycle 1, Day 1, and at subsequent visits if the patient experiences a >5% change in body weight from the weight used for the most recent BSA calculation.

Patients receive MLN4924 diluted with 5% dextrose in a 250-mL IV bag via a 60-minute infusion. MLN4924 should be administered through central or peripheral venous access. The infusion can be slowed or stopped and restarted for any associated infusion reactions. The total infusion time must not exceed six hours from the time of reconstitution.

The entire content of the MLN4924 IV bag will be infused at a constant rate over 1 hour. To ensure that all the MLN4924 enters the body, the infusion line will be flushed with 5% dextrose immediately after administration.

Instructions for the administration of azacitidine are provided in the azacitidine (VIDAZA®) package insert.

Although DLTs can occur at any point during treatment, only DLTs occurring during Cycle 1 of treatment will necessarily influence decisions regarding dose escalation, expansion of a dose level, or evaluation of intermediate dose levels. Patients are monitored through all cycles of therapy for treatment-related toxicities.

The duration of cycles will be 28 days. Azacitidine will be administered in a 5-on/2-off/2-on schedule, i.e., on Days 1, 2, 3, 4, 5, 8, and 9. MLN4924 will be administered on Days 1, 3, and 5. Patients will receive both agents on Days 1, 3 and 5. MLN4924 can be administered at a dose of 20 mg/m$^2$, 30 mg/m$^2$, 40 mg/m$^2$, 45 mg/m$^2$, 50 mg/m$^2$, 60 mg/m$^2$, or 75 mg/m$^2$. Azacitidine will be administered either IV or SC at a dose of 75 mg/m$^2$.

In an optional embodiment, MLN4924 will be administered on Days 1, 8, and 15.

Optionally, the duration of cycles will be 28 days, with the exception of Cycle 1, where a 7-day lead-in will be incorporated where no azacitidine will be administered, such that Cycle 1 will last a total of 35 days. According to this schedule, azacitidine will be administered in a 5-on/2-off/2-on schedule; on Days 8 to 12 and Days 15 and 16 in Cycle 1, and on Days 1, 2, 3, 4, 5, 8, and 9 for all subsequent cycles. According to this schedule, MLN4924 will be administered on Days 1, 3, and 5.

In an another optional embodiment, MLN4924 will be administered on Days 1, 4, 11 and 15 for Cycle 1 only, giving one 35 day cycle; in all subsequent cycles, MLN4924 will be administered on Days 1, 3, and 5, each cycle lasting 28 days. According to this optional schedule, patients will receive both agents on Days 11 and 15 of Cycle 1 and on Days 1, 3, and 5 of subsequent cycles. MLN4924 will be administered at a dose of 20 mg/m$^2$, 30 mg/m$^2$, 40 mg/m$^2$, 45 mg/m$^2$, 50 mg/m$^2$, 60 mg/m$^2$, or 75 mg/m$^2$. Azacitidine will be administered either IV or SC (physician's choice) at a dose of 75 mg/m$^2$.

Patients will receive azacitidine as either an IV or SC injection (see azacitidine [VIDAZA®] package insert for details on administration). On days where both MLN4924 and azacitidine are to be administered, infusion of MLN4924 will commence at a time ranging from 15 to 60 minutes after completion of administration of azacitidine. An assessment of vital signs will be made pre azacitidine dose, pre MLN4924 dose, and post MLN/1924 dose on these days.

What is claimed is:

1. A method of treating cancer comprising, administering to a patient in need of such treatment a therapeutically effective total amount of an NAE inhibitor or a pharmaceutically acceptable salt thereof, and a hypomethylating agent or a pharmaceutically acceptable salt thereof.

2. The method of claim 1, wherein the hypomethylating agent is azacitidine or decitabine, or a pharmaceutically acceptable salt thereof.

3. The method of claim 2, wherein the hypomethylating agent is azacitidine or a pharmaceutically acceptable salt thereof.

4. The method of claim 2, wherein the hypomethylating agent is decitabine or a pharmaceutically acceptable salt thereof.

5. The method of claim 1, wherein the NAE inhibitor is ((1S,2S,4R)-4-(4-((1S)-2,3-dihydro-1H-inden-1-ylamino)-7H-pyrrolo[2,3-d]pyrimidin-7-yl)-2-hydroxycyclopentyl) methyl sulfamate or {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate, or a pharmaceutically acceptable salt thereof.

6. The method of claim 5, wherein the NAE inhibitor is ((1S,2S,4R)-4-(4-((1S)-2,3-dihydro-1H-inden-1-ylamino)-7H-pyrrolo[2,3-d]pyrimidin-7-yl)-2-hydroxycyclopentyl) methyl sulfamate or a pharmaceutically acceptable salt thereof.

7. The method of claim 5, wherein the NAE inhibitor is {(1S,2S,4R)-4-[(6-{[(1R,2S)-5-chloro-2-methoxy-2,3-dihydro-1H-inden-1-yl]amino}pyrimidin-4-yl)oxy]-2-hydroxycyclopentyl}methyl sulfamate, or a pharmaceutically acceptable salt thereof.

8. The method of claim 6, wherein ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or pharmaceutically acceptable salt thereof is administered on each of Days 1, 3, and 5 of a 28-day cycle.

9. The method of claim 8, wherein ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or pharmaceutically acceptable salt thereof is administered at a dose of about 20 $mg/m^2$.

10. The method of claim 8, wherein ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or pharmaceutically acceptable salt thereof is administered at a dose of about 30 $mg/m^2$.

11. The method of claim 8, wherein ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or pharmaceutically acceptable salt thereof is administered at a dose of about 40 $mg/m^2$.

12. The method of claim 8, wherein ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or pharmaceutically acceptable salt thereof is administered at a dose of about 50 $mg/m^2$.

13. The method of claim 8, wherein ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or pharmaceutically acceptable salt thereof is administered intravenously.

14. The method of claim 8, wherein ((1S,2S,4R)-4-(4-((1S)-2,3-dihydro-1H-inden-1-ylamino)-7H-pyrrolo[2,3-d]pyrimidin-7-yl)-2-hydroxycyclopentyl)methyl sulfamate or pharmaceutically acceptable salt thereof is administered subcutaneously.

15. The method of any one of claim 1, wherein the hypomethylating agent is azacitidine or a pharmaceutically acceptable salt thereof and is administered on each of Days 1, 2, 3, 4, 5, 8 and 9 of a 28-day cycle.

16. The method of claim 15, wherein the azacitidine or pharmaceutically acceptable salt thereof is administered at a dose of about 75 $mg/m^2$.

17. The method of claim 15, wherein the azacitidine or pharmaceutically acceptable salt thereof is administered subcutaneously.

18. The method of claim 15, wherein the azacitidine or pharmaceutically acceptable salt thereof is administered intravenously.

19. The method of claim 1, wherein the NAE inhibitor or pharmaceutically acceptable salt thereof is administered in combination with the hypomethylating agent or pharmaceutically acceptable salt thereof in a single dosage form.

20. The method of claim 1, wherein the NAE inhibitor or pharmaceutically acceptable salt thereof is administered in combination with the hypomethylating agent or pharmaceutically acceptable salt thereof in separate dosage forms.

21. The method of claim 1, wherein the cancer is a hematologic malignancy.

22. The method of claim 21, wherein the cancer is acute myeloid leukemia (AML).

23. The method of claim 21, wherein the cancer is myelodysplastic syndromes (MDS).

24. The method of claim 23, wherein the myelodysplastic syndromes (MDS) are diagnosed as any of refractory anemia (RA), refractory anemia with ringed siderblasts (RARS), (refractory anemia with excess blasts (RAEB), and RAEB in transformation (RAEB-T).

25. The method of claim 24, wherein the diagnosis is predominantly one type of myelodysplastic syndromes.

26. The method of claim 24, wherein the diagnosis is more than one type of myelodysplastic syndromes.

27. The method of claim 21, wherein the cancer is diagnosed as any of chronic myelogenous leukemia (CML), acute lymphoblastic leukemia (ALL), chronic lymphocytic leukemia (CLL), Hodgkin's disease (HD), non-Hodgkin's lymphoma (NHL), T-cell lymphoma, multiple myeloma (MM), Waldenstrom's macroglobulinemia, myelodysplastic syndromes (MDS), and myeloproliferative syndromes.

28. The method of claim 27, wherein the diagnosis is predominantly one type of cancer.

29. The method of claim 27, wherein the diagnosis is more than one type of cancer.

30. A kit for treating cancer in a subject in recognized need thereof comprising:

at least one medicament comprising at least one dose of an NAE inhibitor or a pharmaceutically acceptable salt thereof, and at least one medicament comprising at least one dose of a hypomethylating agent or a pharmaceutically acceptable salt thereof;

said kit for treating cancer further comprising dosing instructions for administering the medicaments for treatment of the subject in recognized need thereof.

* * * * *